United States Patent [19]

Cassel

[11] Patent Number: 5,553,321

[45] Date of Patent: Sep. 10, 1996

[54] EYEGLASSES VISOR AND CASE

[76] Inventor: Steven B. Cassel, 60 Mirabel, Mill Valley, Calif. 94941

[21] Appl. No.: 323,493

[22] Filed: Oct. 13, 1994

[51] Int. Cl.[6] .............................. B65D 85/38; G02C 3/02
[52] U.S. Cl. ............................................ 2/13; 206/5
[58] Field of Search ........................ 2/13, 12, 10, 209.13, 2/209.12; 206/5; 351/158

[56] References Cited

U.S. PATENT DOCUMENTS

| | | | |
|---|---|---|---|
| 2,262,142 | 11/1941 | Karmsen | 206/5 X |
| 4,606,453 | 8/1986 | Burns | 2/13 X |
| 5,113,529 | 5/1992 | Carr | 2/13 |
| 5,299,682 | 4/1994 | Tatar | 206/5 |

Primary Examiner—Peter Nerson

[57] ABSTRACT

The present invention entails a sun visor and eyeglasses case adapted to be attached to the temples of a pair of eyeglasses. In particular the sun visor is constructed of two plies of pliable material in an overlying relationship. Unattached ends of the sun visor in combination with an opening in the lower ply enables temple arms to be inserted between layers conveniently, thus forming a stable connection. The opening in the lower ply of material allows the lenses of eyeglasses to be inserted directly into the protective space between the plies without separating the eyeglass arms from sun visor. The sun visor may also serve as an eyeglasses float.

2 Claims, 2 Drawing Sheets

EYEGLASSES VISOR AND CASE

BACKGROUND—FIELD OF THE INVENTION

This invention relates to sun visors that can be attached to eyeglass temples via an insertion mechanism, specifically to such sun visors that are constructed of two overlying plies that form a pocket into which the eyeglasses may be directly inserted and safely stored.

BACKGROUND—DESCRIPTION OF PRIOR ART

Many attempts, in the past, have been made to provide the ultimate sun visor. The goal has now been met to provide a convenient, durable, light weight, and versatile visor that serves as an eyeglasses case when off the head.

U.S. Pat. No. 4,606,453 was the first to provide a visor attached to eyeglasses constructed of two plies of material to form a pocket to protect an individuals eyeglasses, yet it had some noteworthy drawbacks. Latter U.S. Pat. No. 5,113,529 improved upon some of these drawbacks by providing a more stable means of attachment to eyeglasses that allowed use of lighter materials and provided greater stability allowing the visor to be worn during active use. Improving the means of attachment was a significant step towards creating a better visor, but the transition from visor to case remained inconvenient. U.S. Pat. No. 5,113,529 did not combine the new advantageous means of attachment with the added versatility afforded by the complementary functions of having a visor that can serve as a glasses case when needed as such.

OBJECTS AND ADVANTAGES

Accordingly, besides the object and advantages of combining increased stability and lighter materials allowed by an improved attachment mechanism and the versatility provided by combining a sun visor and eyeglasses case into a single product, several objects and advantages of the present invention are;

(a) to provide a sun visor that may be transformed directly into an eyeglasses case without first separating eyeglasses from sun visor;

(b) to provide a visor that may float the sunglasses if dropped in the water;

(c) to provide a unique product that combines the advantages stated above in part (a) and (b) so that eyeglasses need never be separated from visor and thus vulnerable to being lost overboard;

(d) to provide a compact pocket between the plies that only accepts the lenses of the eyeglasses and therefore does not need to be large enough to accept the temple arms of the eyeglasses when folded across the lenses of the eyeglasses, allowing a sleeker, more aerodynamic appearance;

(e) to provide a releasable means of attachment that is fixed to either side of the horizontal slit that decreases the volume of the pocket when closed and thus further contributing to the sleek aerodynamic appearance when eyeglasses are being stored between the plies;

(f) to provide lens only storage which keeps eyeglasses safer when stored in case than cases that do not protect the ends of the temple arms from damaging the inside surface of the eyeglass lens.

(g) to provide a convenient connection mechanism that allows the user to attach eyeglasses to visor without having to weave temple arm through a series of slits by making use of the two ply construction that allows temple arms to be inserted securely between the plies by simply pushing ends of temple arms through the opening in the lower ply and out the end of the sun visor where the ends are left substantially unattached.

DETAILED DESCRIPTION OF THE INVENTION

Figure 1:
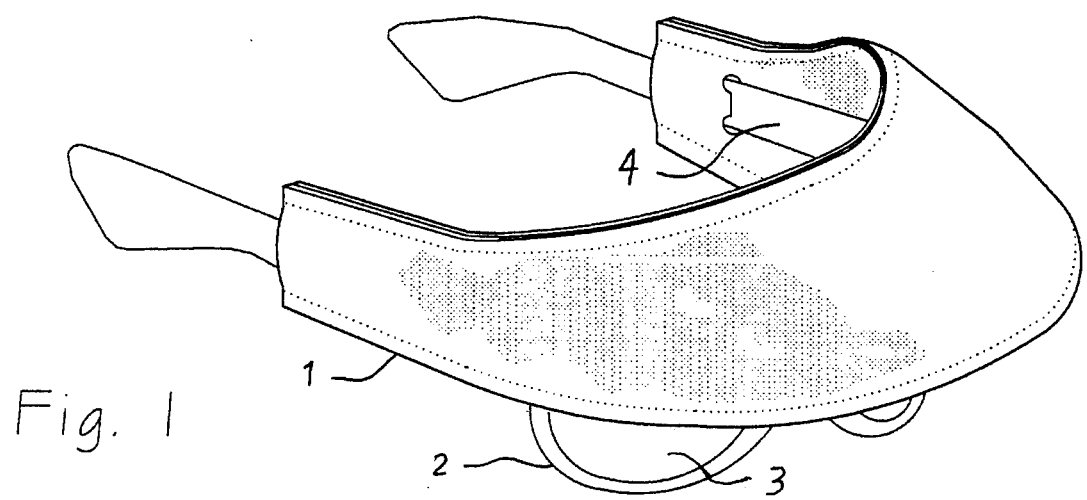
FIG. 1 is a perspective view of the sun visor according to the instant invention wherein the sun visor and case is seen attached to a pair of eyeglasses.

Referring now in more detail to the drawings in which the numerals indicate parts throughout the several views, FIG. 1 illustrates the eyeglasses visor and case (1) mounted to a pair of eyeglasses (2). The view shows how the arms of the sun glasses insert betweeen the plies. The eyeglasses are of conventional design and include lenses (3) and foldable arms (4).

Figure 2:
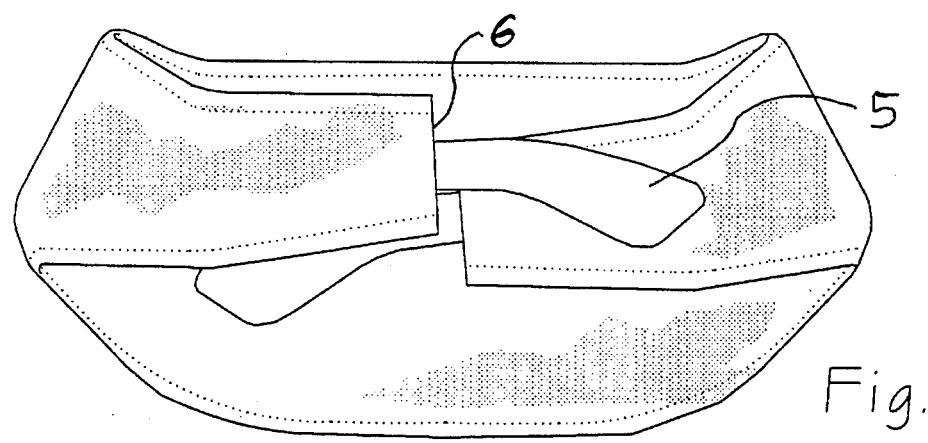
FIG. 2 is a bottom view that illustrates the eyeglasses visor and case mounted to the limbs of a pair of eyeglasses, with the limbs folded across the lenses of eyeglasses and lenses have been stored in pocket between the plies.

FIG. 2 illustrates the visor functioning as an eyeglasses case. The ends of the sun glasses arms (5) can be seen protruding from the open ended sides (6) of the visor/case. The FIG. 2 shows how the lenses of the eyeglasses are stored separately from the eyeglasses arms providing a safer and more compact product.

Figure 3:
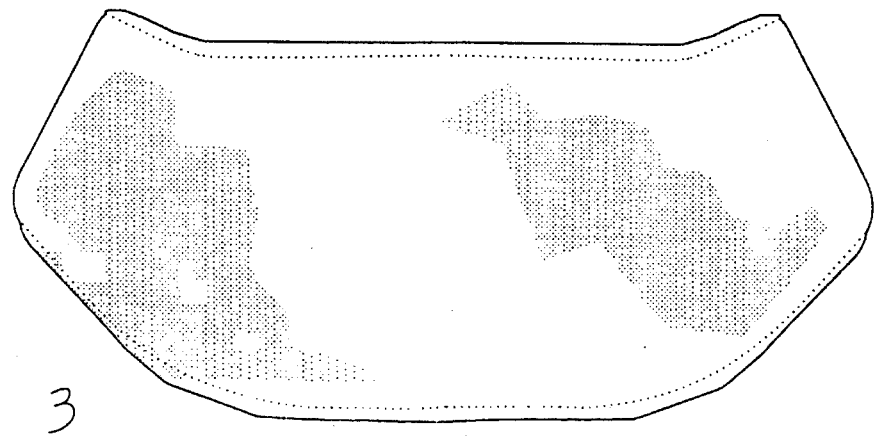
FIG. 3 illustrates the top view of the eyeglasses visor and case with the visor and case mounted to the limbs of pair of eyeglasses, with the lenses stored in the pocket between the plies.

FIG. 3 is a top view of the visor/case when functioning as an eyeglasses case.

Figure 4:
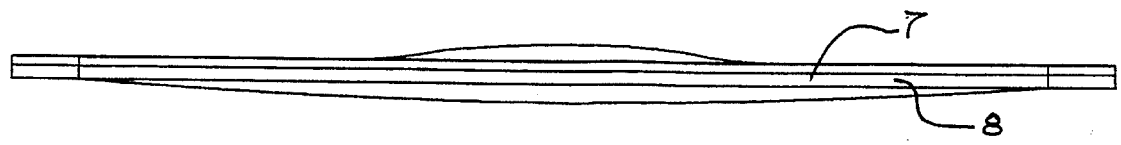
FIG. 4 is a front elevational view of the eyeglasses visor and case.

FIG. 4 illustrates the two plied construction of the case/visor that is composed of an upper (8) and a lower (7) plie of material.

Figure 5:
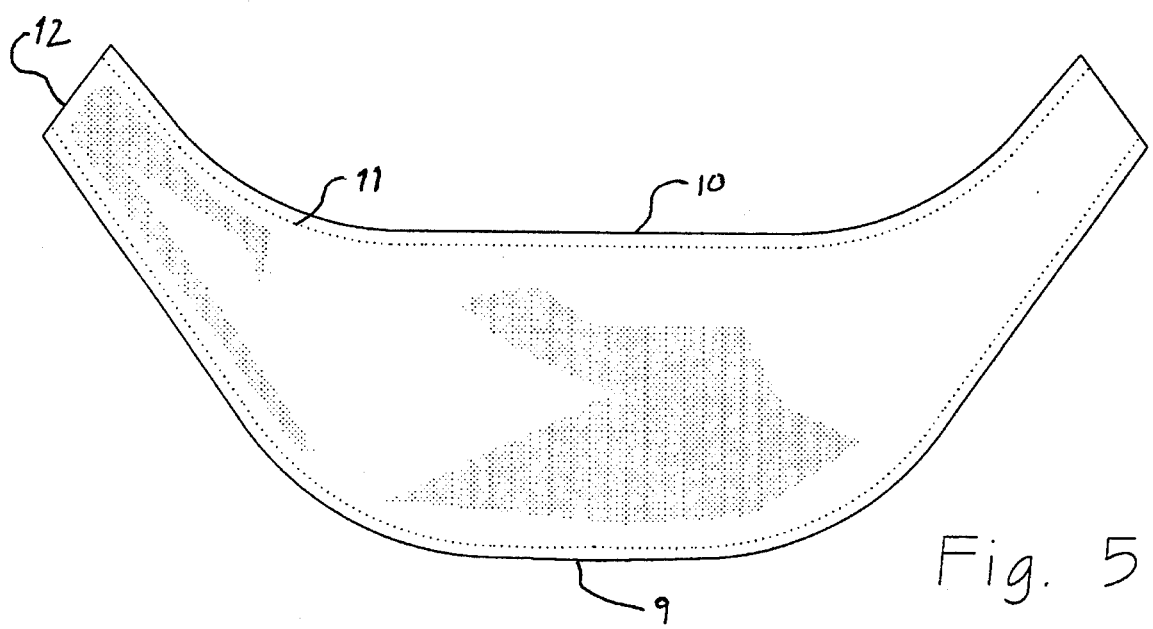
FIG. 5 is a top view of the sun visor and eyeglasses case.

FIG. 5 shows the visor/case unattached to eyeglasses from the top view. The plies of material are identical in shape, each including a front convex edge (9) and a concave rear edge (10) that rests adjacent to forehead when being used as a visor. Both the convex and concave edges are attached together along their lengths as by stitching (11) or adhesive. A small area at either end of the visor is left unattached (12) to allow, for the arm of the eyeglasses to pass out from between layers. The concave and convex sides meet to form a right and left side which corresponds in size to a distance slightly wider than the eyeglass arm width of a typical pair of eyeglasses.

Figure 6:
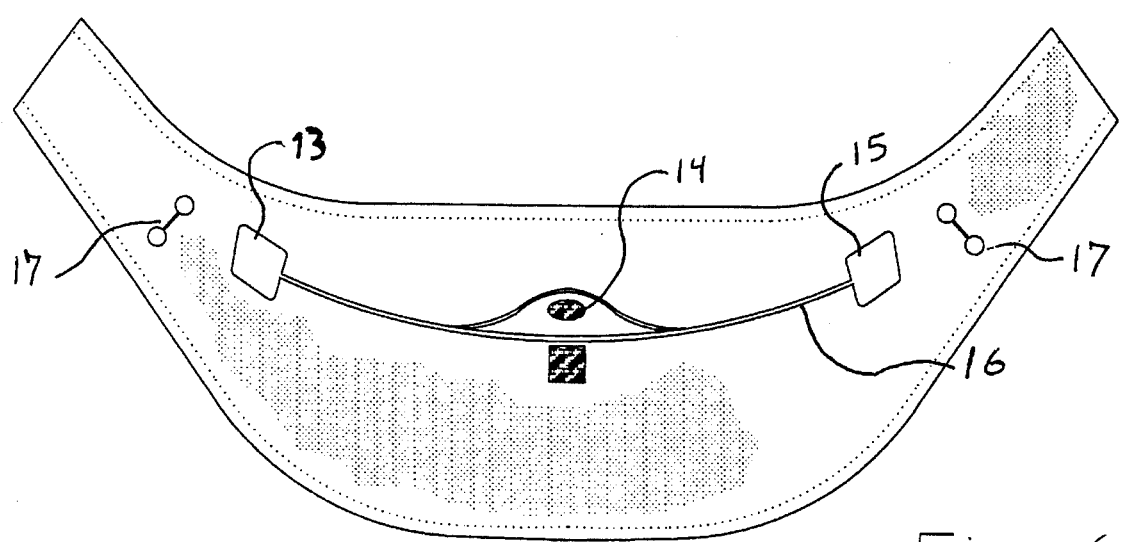
FIG. 6 is a bottom view of the sun visor and eyeglasses case illustrating how the lower ply can be pulled back to accept eyeglasses into the pocket between the plies.

FIG. 6 is a view of the underside of the visor/case that illustrates the slit in the lower ply (16) that allows the eyeglasses to be inserted directly between the upper and lower plies. This unique design eliminates the need to detach eyeglasses from visor between functions. The slit is greater in length to the distance between the temples of a normal pair of eyeglasses to allow the lenses to pass through the slit into the protective space between the plies. A releasable fastener element (14) is attached intermediate the ends of the slit in the lower ply to secure eyeglasses when in case.

The visor is constructed from flexible lightweight durable materials that may be buoyant to float any standard weight eyeglasses. The ends of the horizontal slat (13 and 15) are rounded to distribute the stress equally along a curve to prevent the ends of the lower plied from ripping when glasses are being inserted between the plies.

The releasable fastening element that connects the opposing sides of the lower plied to secure eyeglasses in the pocket may be attached to the opposing sides of the slit in such a manner that the size of the pocket decreases when the elements are connected.

To attach the sun visor to eyeglasses the ends of the temple arms are pushed between the layers at each end of the horizontal slit (13,15) or if the arms of the eyeglasses are particularly thin through the smaller slit (17). Then the ends of the eyeglass arms are pushed out through the ends of the sun visor that are not attached. After the temple arms have been inserted, the sun visor may be slid forward or backward on the temple arms to comfort.

To insert the glasses between the plies, the lower ply need only be pulled back to allow the eyeglass lenses to be directly inserted into the pocket between the plies; the releasable fastening elements (14) may be attached to secure eyeglasses in case.

SUMMARY RAMIFICATIONS AND SCOPE

The reader will see that the design of a sun visor as previously described provides a simply superior sun visor. Versatile, cost effective, light weight, and durable construction meets all the essential requirements of the active individual. Great versatility is achieved by a two plied construction that combines complementary functions allowing this product to serve as a sun visor while on the face and as an eyeglasses case when off the face. This product keeps eyeglasses afloat both in and out of the case and even between functions making it a true must for water enthusiasts.

Unmatched convenience is made possible by two unique design features. Direct entry design allows eyeglasses to be directly inserted between the protective plies without having to separate temple arms from the sun visor. A unique connection mechanism provides all the structural security, previously achieved by an inconvenient weaving technique, by simply inserting temple arms between plies. Extend the lifetime of your eyeglasses by protecting them from scratches and loss while protecting your outlook on the future, by keeping your eyes in the shade.

Although the description above contains many specificities, these should not be construed as limiting the scope of the invention but as merely providing illustrations of some of the presently preferred embodiments of this invention. For example, the object of designing a sun visor that allows the eyeglass lenses to be directly inserted between protective plies without having to first detach the eyeglasses from visor can be achieved many different ways. A number of different shaped slits in the lower ply and various releasable means of attachment can accomplish the same objective.

Thus the scope of the invention should be determined by the appended claims and their legal equivalents, rather than by the example given.

I claim:

1. A sun visor and eyeglasses case for attaching to the temples of eyeglasses comprising:

a) a two ply crescent shaped bill member secured in an overlying relationship along respective perimeters thereof, each bill member having a concave edge forming a back side for placement adjacent to the forehead of an individual and a convex edge forming a front side wherein the concave and convex edges of the respective bill members terminate to form respective right and left sides;

b) a first slit in the lower ply adapted to allow eyeglasses to pass through the slit to be stored between the plies, wherein a lower ply of said bill member detaches from an upper ply providing direct lens only storage, second slit means in the lower ply located on opposite sides of said first slit whereby the temple arms do not need to be separated from the visor between deployed and stored configurations.

2. The visor of claim 1 further comprising a releasable attachment means to temporarily attach the opposing sides of the slit in the lower ply to secure the lenses of eyeglasses between the upper and lower plies to provide a case storage means for the lenses.

* * * * *